US012773507B2

(12) United States Patent
Borm

(10) Patent No.: US 12,773,507 B2
(45) Date of Patent: Oct. 27, 2026

(54) VENTILATOR HAVING TWO SERIAL BLOWERS

(71) Applicant: Loewenstein Medical Technology S.A., Luxembourg (LU)

(72) Inventor: Petrus Johannes Josephus Borm, Eindhoven (NL)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 712 days.

(21) Appl. No.: 18/203,133

(22) Filed: May 30, 2023

(65) Prior Publication Data

US 2023/0390511 A1 Dec. 7, 2023

(30) Foreign Application Priority Data

Jun. 1, 2022 (DE) ......................... 102022113882.8

(51) Int. Cl.
*A61M 16/00* (2006.01)

(52) U.S. Cl.
CPC .... *A61M 16/0066* (2013.01); *A61M 16/0006* (2014.02); *A61M 16/0009* (2014.02); *A61M 16/0069* (2014.02); *A61M 16/024* (2017.08); *A61M 2205/3334* (2013.01); *A61M 2205/3344* (2013.01); *A61M 2205/3355* (2013.01); *A61M 2205/3368* (2013.01)

(58) Field of Classification Search
CPC .......... A61M 16/0006; A61M 16/0009; A61M 16/0057; A61M 16/0066; A61M 16/0069; A61M 16/024; A61M 2205/3334; A61M 2205/3344; A61M 2205/3355
See application file for complete search history.

(56) References Cited

U.S. PATENT DOCUMENTS 6,209,540 B1 * 4/2001 Sugiura ............. A61M 16/0006 128/205.24
9,408,991 B2 8/2016 Nitta et al.
2003/0015200 A1 * 1/2003 Hansen ............... A61M 16/026 128/204.18
2006/0113690 A1 * 6/2006 Huddart ............ A61M 16/1075 261/129
2007/0199566 A1 * 8/2007 Be'eri ................. A61M 16/024 128/204.23
2012/0234323 A1 * 9/2012 Connor ............. A61M 16/0066 128/205.25
2014/0116441 A1 * 5/2014 McDaniel ......... A61M 16/0465 128/205.24
2018/0043116 A1 2/2018 Birnkrant et al.
2018/0200463 A1 * 7/2018 Liu ................... A61M 16/0066
(Continued)

FOREIGN PATENT DOCUMENTS

DE 102018100473 B4 * 3/2021 ............... A62B 7/10
EP 3501583 A1 6/2019

*Primary Examiner* — Joseph D. Boecker
(74) *Attorney, Agent, or Firm* — Abel Schillinger, LLP

(57) ABSTRACT

Ventilator for the ventilation of a living being, comprising at least a gas module and a control module, the gas module comprising at least two blowers for generating a positive pressure and/or a negative pressure and at least one connector for connection to a hose, and the control module comprising at least a control unit for controlling the gas module. At least a first blower has an opposite delivery direction to the at least second blower.

19 Claims, 3 Drawing Sheets

(56) References Cited

U.S. PATENT DOCUMENTS

| | | | | |
|---|---|---|---|---|
| 2019/0269966 | A1* | 9/2019 | Tiemann | A61M 16/024 |
| 2019/0298947 | A1* | 10/2019 | Trivikram | A61H 9/0078 |
| 2021/0290876 | A1* | 9/2021 | Trivikram | A61M 16/0833 |
| 2021/0308400 | A1* | 10/2021 | Sipes, Jr. | G16H 20/40 |
| 2022/0143353 | A1 | 5/2022 | Oddo | |
| 2024/0058563 | A1* | 2/2024 | Ruppell, III | A61M 16/206 |
| 2024/0277966 | A1* | 8/2024 | Rapoport | A61M 16/1005 |

* cited by examiner a)

b)

VENTILATOR HAVING TWO SERIAL BLOWERS

CROSS-REFERENCE TO RELATED APPLICATIONS

The present application claims priority under 35 U.S.C. § 119 of German Patent Application No. 102022113882.8, filed Jun. 1, 2022, the entire disclosure of which is expressly incorporated by reference herein.

BACKGROUND OF THE INVENTION

1. Field of the Invention

The invention relates to a ventilator having two blowers and to a method for operating a ventilator having two blowers.

2. Discussion of Background Information

Ventilators having a blower, by means of which pressure can be built up only in one direction, are known in the prior art. In the general case a positive pressure, which is used for the ventilation of patients, is generated by this one blower. Complicated pneumatic arrangements, in which a negative pressure can also be generated by a circuit of different valves, are furthermore known. These, however, require a high control complexity in order to control the large number of valves correctly. Such a switchover also allows only an abrupt variation of the pressure conditions, that is to say the positive pressure currently prevailing is changed directly into a likewise large negative pressure when the valves are switched.

In view of the foregoing it would be advantageous to have available a ventilator that offers both ventilation under subatmospheric pressure and ventilation under superatmospheric pressure.

SUMMARY OF THE INVENTION

The present invention provides a ventilator for the ventilation of a living being, comprising at least a gas module and a control module, the gas module comprising at least two blowers for generating a positive pressure and/or a negative pressure and at least one connector for connection to a hose, and the control module comprising at least a control unit for controlling the gas module. The ventilator is one wherein at least a first blower has an opposite delivery direction to the at least second blower.

In some embodiments, the ventilator is one wherein the at least two blowers are connected to one another via their outlet ports.

In some embodiments, the ventilator is one wherein the at least two blowers are connected to one another via their intake ports.

In some embodiments, the ventilator is one wherein at least a first blower is arranged so that the blower at least temporarily generates a positive pressure on the side of the connector, and at least a second blower is arranged so that the blower at least temporarily generates a negative pressure on the side of the connector.

In some embodiments, the ventilator is one wherein during the generation of a positive pressure on the side of the connector by at least one of the blowers, the at least one other blower with an opposite delivery direction is off and/or runs at a rotational speed that is less than that of the one blower and/or generates a lower pressure than the one blower.

In some embodiments, the ventilator is one wherein during the generation of a negative pressure on the side of the connector by the other blower, the at least one blower with an opposite delivery direction is off and/or runs at a rotational speed that is less than that of the other blower and/or generates a lower pressure than the other blower.

In some embodiments, the ventilator is one wherein at least one of the blowers is adapted to generate a negative pressure.

In some embodiments, the ventilator is one wherein the ventilator is adapted to provide ventilation with a negative expiratory pressure.

In some embodiments, the ventilator is one wherein the ventilator is adapted to generate a constant expiratory flow, a negative expiratory pressure being provided by means of one of the blowers in the course of the expiration.

In some embodiments, the ventilator is one wherein the ventilator is adapted to carry out a cough therapy, a patient being provided with a breathing gas at positive pressure by the one blower during the inspiration, and after the end of the inspiration a rapid switchover being made to a breathing gas at negative pressure, provided by the other blower.

In some embodiments, the ventilator is one wherein the ventilator is adapted to provide superimposed and/or oscillating ventilation.

In some embodiments, the ventilator is one wherein the one blower determines the ventilation frequency and the other blower generates the superimposed frequency.

In some embodiments, the ventilator is one wherein the ventilator is adapted to provide superimposed ventilation and ventilation with a negative expiratory pressure simultaneously.

In some embodiments, the ventilator is one wherein at least one gas source is arranged between the connector and the blowers, at least one gas from the gas source being introduced via at least one valve into the breathing gas delivered by one of the blowers.

In some embodiments, the ventilator is one wherein a mixing region for better mixing of the breathing gas that is delivered and the gas that is introduced through the valve is arranged in the region of the valve.

It is to be pointed out that the features mentioned individually in the claims may be combined with one another in any desired technically expedient way and represent further configurations of the invention. The description additionally characterizes and specifies the invention particularly in connection with the figures.

It is furthermore pointed out that a conjunction "and/or" used herein, standing between two features and linking them, is always to be interpreted as meaning that in a first configuration of the subject matter according to the invention only the first feature may be present, in a second configuration only the second feature may be present, and in a third configuration both the first and the second feature may be present.

A ventilator is intended to mean any apparatus that assists a user or patient with natural breathing, takes over the ventilation of the user or living being (for example a patient and/or newborn and/or premature baby) and/or is used for breathing therapy and/or influences the breathing of the user or patient in another way. This includes, for example but not exclusively, CPAP and BiLevel apparatuses, narcotic or anesthetic apparatuses, breathing therapy apparatuses, (clinical, out-of-clinic or emergency) ventilator apparatuses, high-flow therapy es and cough machines. Ventilator apparatuses may also be understood as diagnostic es for ventilation. Diagnostic apparatuses may in this case be used generally to record medical and/or breathing-related parameters of a living being. This also includes apparatuses that can record and optionally process medical parameters of patients in combination with the breathing or exclusively relating to breathing, for example simulators.

A patient interface may, unless otherwise expressly described, be understood as any peripheral apparatus that is intended for interaction, in particular for therapeutic or diagnostic purposes, of the measuring instrument with a living being. In particular, a patient interface may be understood as a mask of a ventilator or a mask connected to the ventilator. The mask may be a full-face mask, that is to say covering the nose and mouth, or a nasal mask, that is to say a mask enclosing only the nose. Tracheal tubes or cannulas and so-called nasal cannulas can also be used as a mask, or patient interface. In some cases, the patient interface may also be a simple mouthpiece, for example a hose, through which the living being at least exhales and/or inhales.

In the course of the description, ventilation and therapy are to be understood as synonyms, unless otherwise explicitly indicated. Occasionally, a therapy may also be understood as the single and/or recurring performance of a maneuver, for example a recruiting maneuver and/or a cough maneuver.

The ventilator according to the invention is, in particular, one wherein at least two blowers are connected in series, at least two blowers having an opposite delivery direction. By means of such an arrangement, several advanced forms of ventilation or therapy may be offered. For example, besides a ventilation mode, the ventilator may also be used as a cough machine (insufflation, exsufflation), or to assist coughing. It also allows a negative expiratory pressure during the ventilation. Provision may furthermore be made that superimposed ventilation and/or high-frequency-oscillating ventilation is also possible.

In some embodiments, blowers that can achieve a high rotational speed and/or flow and/or pressure within a very short time are provided. With the use of such highly responsive blowers, in some embodiments the number of valves may in some cases be reduced and the response time of the ventilator may sometimes be additionally improved.

In some embodiments, an additional gas path is provided in the gas module, in order to connect a 2-hose system to the system, the inspiratory or expiratory branch being opened or closed by means of one or more valves after each breathing phase.

In some embodiments, additional control valves are arranged, for instance in order to be able to control a hose system with a patient valve. The control pressure may in this case, for example, likewise be generated by at least one of the blowers.

BRIEF DESCRIPTION OF THE DRAWINGS

The invention will be described in more detail by way of example with the aid of FIGS. 1 to 3.

In the drawings.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
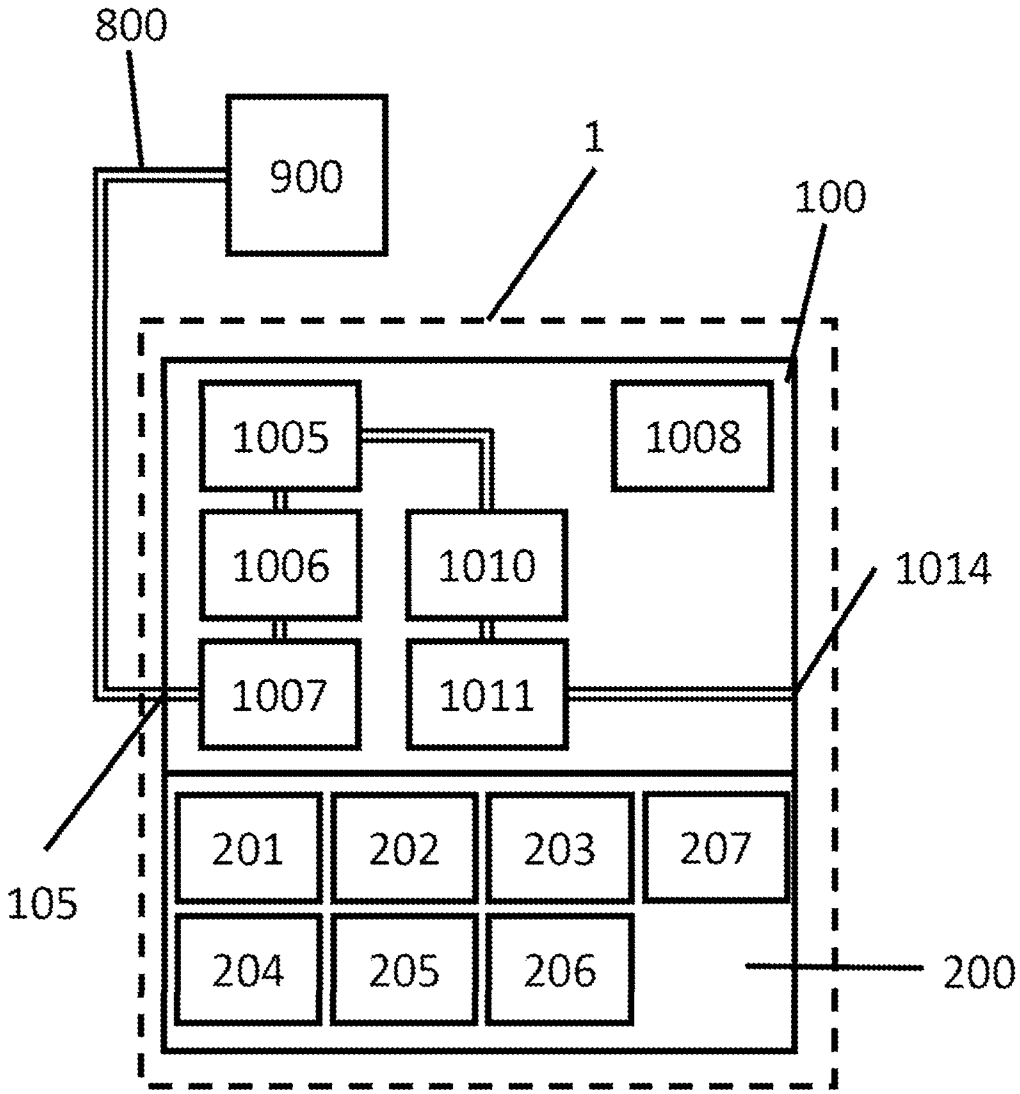
FIG. 1 schematically shows an exemplary embodiment of the ventilator of the invention.

FIG. 1 shows a schematic representation of an exemplary embodiment of the ventilator 1. For example, the ventilator 1 is subdivided into a gas module 100 and a control module 200. The control module is adapted and configured to control the gas module 100.

For example, the ventilator 1 is connected via a connection 800 to a patient 900. Via the connection 800, a gas-conducting connection may be established between the ventilator 1 and the patient 900, for example via the connector 105 of the gas module 100. The connection 800 may, for example, be configured as a ventilator hose and/or hose system. The connection to the patient 900 is for instance achieved by a patient interface, for example a ventilator mask or a tube.

The gas module 100 of the ventilator 1 comprises for example a blower 1010 for generating a positive pressure in the patient's airways, a blower 1011 for generating a negative pressure in the patient's airways, and a sensor system for determining the gas parameters inside the gas module 100. By the blower 1010, the ventilator 1 is adapted and configured to carry out a positive pressure ventilation of the patient 900, in order to assist the breathing of the patient 900 and/or to ventilate the patient 900, that is to say substantially to dictate the ventilation of the patient 900. The blower 1010 is furthermore adapted, for example, to take in ambient air as breathing gas and deliver it in the direction of the patient 900. Provision may also be made that a synthetic breathing gas is provided, for example from compressed gas cylinders or a compressed gas line.

At this point, it should be noted that although blowers may build up a pressure in one direction, the gas flow through a blower may quite possibly take place in two directions. So that a gas flow takes place via the blower 1010 in the pressure direction, that is to say in the direction of the patient 900, the blower 1010 must overcome the counter pressure—generated for example by the patient 900—that is to say it must provide a higher pressure than the patient 900.

The sensor system, for example comprising at least one pressure sensor 1005, a flow sensor 1006, a temperature sensor 1007, is adapted and configured to record measurement values of the gas in the gas module 100. The measurement values relate for example to pressure, flow rate, temperature, humidity and/or gas composition. The sensor system is, for example, arranged between the blowers 1010, 1011 and the connector 105. By means of the sensor system, inter alia, conclusions may be drawn regarding the breathing parameters, for example frequency, pressure, flow rate of the patient 900. Provision may also be made that, with the aid of the measurement values recorded by the sensor system, various breathing situations, for instance apnea, snoring, sleeping/waking state, normal breathing, etc. may be identified. In some embodiments, the control module 200 is for example adapted and configured to adjust the ventilation parameters according to the respective breathing situation.

In order to control the gas module 100, the control module 200 comprises a control unit 201, which is configured to control at least the blowers 1010 and 1011. The control unit 201 is furthermore adapted and configured to drive the gas module 100 on the basis of specifications and/or settings and/or calculations for the ventilation and/or breathing of the patient 900.

The control of the gas module 100 is, for example, ensured by means of the control module 200. For this purpose, the control module 200 comprises at least one control unit 201, which is adapted to drive at least the two blowers 1010, 1011. The control may, for example, be carried out with the aid of specifications. In some embodiments, the ventilator 1 may respond to the ventilation situation of the patient 900. For this purpose, the control module 200 may for example comprise a calculation unit 202 which is adapted, with the aid of the specifications and/or recorded sensor values, to determine the ventilation to be achieved.

The control module 200 of the ventilator 1 furthermore comprises for example a sensor unit 204, an evaluation unit 203, an input unit 205 and a memory unit 206. The sensor unit 204 is adapted and configured to receive and optionally process the measurement values recorded by means of the sensor system. The evaluation unit 203 is adapted and configured to evaluate and/or analyze the measurement values received from the sensor unit 204 and optionally processed. For example, provision may be made that the evaluation unit 203 analyzes the measurement values in respect of whether the specified control of the gas module 100 is taking place correctly, for example whether the desired pressures, flow rates and/or volumes are being generated. Provision may also be made that the evaluation unit 203 is configured and adapted to ascertain the breathing parameters of the patient 900 with the aid of the measurement values. Provision may also be made that the evaluation unit 203 identifies breathing situations determined with the aid of the measurement values. The results of the analysis and/or evaluation are, for example, forwarded via the input unit 205 to the calculation unit 202. By means of the calculation unit 202, the analysis results and/or the measurement values may also be incorporated into the determination of the ventilation parameters that form the basis of the control of the gas module 100.

For example, the control module 200 comprises a memory unit 206. Measurement values, analyses and/or evaluations may be stored at least temporarily in the memory unit 206. In some embodiments of the ventilator 1, the measurement values recorded by the sensor system are stored in the memory unit 206.

The input unit 205 is used for example as an interface via which data, values and/or information can be input into the ventilator 1, particularly into the control module 200. In some embodiments, input of data, values and/or information also takes place inside the system via the input unit 205, for example from the evaluation unit 203, to the calculation unit 202. It is also envisioned that the input unit 205 is adapted and configured to forward data, values and/or information to an external apparatus. For example, for this purpose a remote terminal, for instance a computer, notebook, smartphone, server, cloud and/or tablet may be connected to the ventilator 1 via an interface. As an alternative or in addition, a user interface 207, which for example is configured to display data/values/information concerning the ventilation and may also be adapted so that a user can input data/values/information, may also be provided on the ventilator 1. The user interface 207 is, in particular, adapted to input specifications and/or settings concerning the ventilation into the ventilator 1. The calculation unit 202 is, for example, adapted and configured to determine the ventilation parameters with the aid of the specifications and/or settings. The specifications and/or settings comprise, for example but not exclusively, pressure, flow rate, lung volume, gas composition, respiratory rate, tidal volume, type of the living being, age, weight, diseases (in particular respiratory diseases), gas exchange, breathing problems. In some embodiments, the user interface 207 has an input screen, by means of which settings concerning the ventilation, which are transmitted to the control module 200, are input. In some embodiments, a multiplicity of ventilation patterns and/or ventilation programs, which can be accessed via the user interface 207, are stored in the memory unit 206.

In the course of the analysis of the measurement values by the evaluation unit 203, provision may also be made that the control unit 201 and/or the calculation unit 202 can autonomously access preprogrammed ventilation patterns and can carry them out for the ventilation of the patient 900.

In some embodiments, a display of the current ventilation is possible, for example in the form of values and/or graphs, via the user interface 300.

In order to deliver the breathing gas, two blowers 1010, 1011 are arranged in the gas module 100. As an alternative or in addition to the two blowers 1010, 1011, at least one bidirectional pump may also be used.

The delivery directions of the blowers 1010, 1011 are in this case opposite, so that both a positive pressure and a negative pressure can be generated on the side of the connector 105. For example, the blower 1010 functions in order to generate a positive pressure. In this case, a delivery direction means in particular the pressure direction. For example, the blower 1010 builds up a pressure in the direction of the connector 105, or of the patient 900. For this purpose, for example, the blower 1010 takes in gas via the outlet 2014, which as an alternative or in addition may be configured as an intake region, and delivers the gas through the gas module 100 to the connector 105. A negative pressure is generated for example by means of the blower 1011, which is adapted to deliver gas counter to the delivery direction of the blower 1010. Because of the opposite delivery direction, that is to say intake of gas at the connector 105, a negative expiratory pressure may for example be generated for the patient 900.

In particular, the blowers 1010 and 1011 may be driven by means of the control unit 201. For example, in order to generate a negative pressure only the blower 1011 is activated, the latter being arranged so that gas is taken in through the connector 105. Likewise, provision may be made that in order to generate a positive pressure, only the blower 1010, which takes in gas from the outlet 1014, is activated. As an alternative or in addition, provision may be made that both blowers 1010, 1011 are continuously active and run at a rotational speed level and/or pressure level. In some embodiments, it may be advantageous for the two blowers to work against one another in order to achieve a better working point for the blowers. Provision may also be made that the blowers 1010, 1011 are activated or deactivated, depending on the form of ventilation or therapy. If provision is made that a cough therapy is started, for example, the blower 1011 may be activated for the duration of the cough therapy and deactivated again after the end. During the therapy, the blower 1011 runs in the periods of time in which a negative pressure is not intended to be generated, that is to say at a particular rotational speed, the rotational speed being increased in order to generate a negative pressure.

The blowers 1010, 1011 are, for example, adapted and arranged so that gas can flow unimpeded against the delivery direction through the blowers, without the latter being damaged, for example by forced rotation of the delivery wheels counter to the intended direction. In some embodiments, provision is made that bypass lines are arranged in the gas module 100 so that gas can flow past the blowers while the respective blower is deactivated.

While the control unit 201 is adapted to drive the blowers 1010, 1011 so that the specifications for the ventilation are achieved, the ventilation thereby implemented is checked by means of the sensor system, for example by means of the pressure sensor 1005, the flow sensor 1006 and the temperature sensor 1007. The evaluation unit 203 is, for example, adapted and configured to evaluate the measurement values of the sensors 1005, 1006, 1007 and to analyze said values in respect of whether the breathing is being carried out according to the specifications.

For example, the calculation unit 202, optionally in combination with the evaluation unit 203, is adapted and configured to compare the ventilation with the breathing of the patient 900 and to check for deviations. In some embodiments, the calculation unit 202 and/or the control unit 201 is adapted to carry out any corrections of the ventilation automatically. The calculation unit 202 is, for example, adapted and configured also to incorporate gas parameters, for example pressure and/or flow rate and/or temperature and/or gas composition, into the determination of the ventilation parameters. For example, the pressure and/or flow rate generated by the patient 900 is also incorporated in the determination of the ventilation parameters by the calculation unit 202.

The gas module 100 is controlled by means of the control module 200, in particular the control unit 201. The control signals for the control are, for example, derived by means of the calculation unit 202 from particular ventilation parameters. For example, the specifications for the ventilation or therapy are input via the user interface 207. The specifications may for example relate to lung volume, flow rate, pressure, tidal volume, respiratory rate, ventilation or therapy program, size, weight, diseases, etc. of the patient 900. In some embodiments, inputs can be carried out at least in respect of pressure and flow rate of the ventilation or therapy.

Patterns, for example for various forms of ventilation or therapy, may be stored in the memory unit 206. These patterns may, for example, be adjusted. In some embodiments, the ventilation parameters and/or specifications can also be adjusted during the ventilation by means of the user interface 207, for example without interrupting the current ventilation or therapy.

According to the specifications, in a first step the ventilation parameters are determined by the calculation unit 202. Corresponding control signals are derived from the ventilation parameters and transmitted to the control unit 201. With the aid of the control signals, in a second step the control unit 201 controls the gas module 100, for example in order to ventilate the patient 900, to assist with breathing or to carry out another form of therapy, for example a cough maneuver.

The use of two blowers in a ventilator gives rise to additional therapy possibilities with a single apparatus. Besides positive pressure ventilation, a negative expiratory pressure is thus also possible. While one of the blowers 1010, 1011 can generate a positive pressure on the side of the connector 105, or for the patient 900, generation of a negative pressure on the side of the connector 105, or for the patient 900, is also possible because of the opposite pressure direction or delivery direction of the other blower 1010, 1011.

The ventilator 1 is, for example, also adapted to implement flow-controlled ventilation with a negative expiratory flow rate and/or pressure, a constant flow rate being specified during the inspiration and a constant flow rate being specified during the expiration. The ratio between inspiratory and expiratory flow rates is for example 1, that is to say the flow rate during the inspiration corresponds in magnitude to the flow rate of the expiration, the sign being reversed. In order to generate a constant negative flow rate during the expiration, provision is made that a negative pressure can be generated by the second blower 1011, so that a constant flow rate is achieved.

During natural expiration, the flow rate and the pressure generally decrease toward the end of expiration, until the pressure has come to a (positive) minimum. By a further, for example linear, pressure reduction toward negative pressures, assisted by means of the second blower 1011, a constant expiration flow rate may be achieved.

In some embodiments, the ventilator 1 is configured to carry out a cough therapy. In order to allow the patient 900 to cough and/or to trigger a cough from the patient 900 and/or to take over the cough function for the patient 900, the patient is initially allowed to breathe in deeply by means of the blower 1010. After the inspiration, the coughing is carried out by rapid deceleration of the blower 1010 and optional rapid acceleration of the blower 1011. By the rapid reversal of the flow rate and/or pressure, for example, secretion can thus be removed from the airways of the patient 900.

In some embodiments, the ventilator 1 is configured to provide superimposed ventilation. In this case, the ventilation frequency is superimposed with a high frequency in the form of small flow rate and/or pressure changes. Provision may be made that only one blower generates these flow rate and/or pressure changes. In the proposed ventilator 1, however, provision may also be made that for example the blower 1010 generates the respiratory rate, that is to say ventilates the patient 900, while the blower 1011 generates the superimposed frequency. The superimposed ventilation may for example be used together with a tracheal tube, for instance in order to be able to determine further lung and breathing parameters. As an alternative or in addition, properties of the tube and/or in the tube may also be determined by means of the superimposed ventilation. By the two blowers 1010, 1011, the ventilator 1 is also adapted to carry out superimposed ventilation together with a negative expiratory pressure.

In some embodiments, as an alternative or in addition the ventilator 1 is configured to generate a high-frequency oscillation of the pressure. For example, the high-frequency oscillation may be superimposed on a PEEP (positive end-expiratory pressure). While for example the blower 1010 provides the PEEP, the blower 1011 may generate a high-frequency oscillation of the pressure by periodic changes of the rotational speed. In some embodiments, the PEEP together with the high-frequency oscillation of the pressure may be generated by a single blower. A high frequency is in this context, for example, more than 3 Hz. In some embodiments, provision may be made that both blowers contribute to generating the PEEP, for example, and/or both blowers in combination generate the high-frequency oscillation. For example, by combined generation of the high-frequency oscillation by both blowers, a higher frequency and/or amplitude may be achieved. In the case of two blowers that have an opposite delivery direction, if the one blower decelerates while the other blower accelerates, a pressure change is therefore generated in the same direction (higher or lower pressure). By the two blowers connected in series, the frequency generation of the two blowers can therefore be correlated. If for example the one blower has an acceleration of 100 mbar/0.1 sec and the other blower has a deceleration of 100 mbar/0.1 sec, a combined pressure change of the two blowers of 200 mbar/0.1 sec may be achieved. With the ventilator 1 according to the invention, at least an amplitude of the high-frequency oscillation of 50 mbar at 3 Hz may be achieved, and in some embodiments an amplitude of 50 mbar at 5 Hz may be achieved. In some embodiments, at least an amplitude of 100 mbar at 5 Hz may be achieved. With lower amplitudes, in some embodiments even higher frequencies may be achieved.

In some embodiments, provision may additionally be made that bypass lines and valves are arranged so that the two blowers 1010, 1011 can build up a pressure in the same direction. For example, one bypass leads from the outlet 1014 to behind the blower 1010 and a second bypass leads between the blowers 1010, 1011 and behind the blower 1010. The second bypass has in this case ended closer to the connector 105 than the first bypass has. In one valve setting, provision may be made that both the blower 1010 and the blower 1011 take in gas via the connector 105 and deliver it in the direction of the outlet 1014. Thus, the pressure buildup would then take place in the direction of the outlet 1014. In some embodiments, as an alternative or in addition, bypass lines may be arranged in such a way that a combined pressure buildup of the blowers 1010, 1011 in the direction of the connector 105 is also possible.

Figure 2:
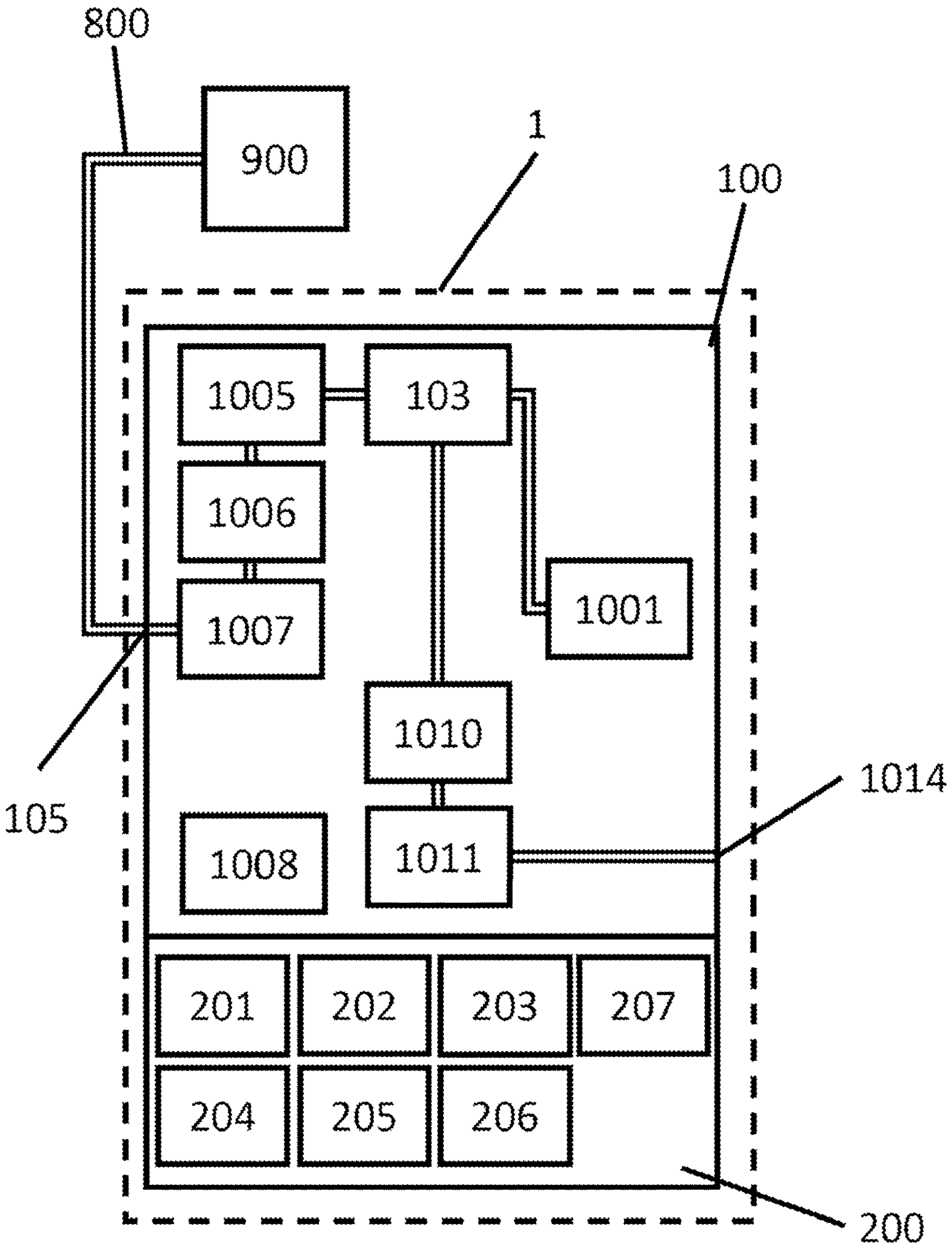
FIG. 2 schematically shows another exemplary embodiment of the ventilator of the invention.

FIG. 2 schematically represents another exemplary embodiment of the ventilator 1. The construction with two blowers 1010, 1011 is in this case supplemented with at least one gas source 1001. By means of the gas source 1001, additional gas may be mixed with the breathing gas that is delivered. For example, provision may be made that the gas source 1001 is configured as an oxygen source. By means of the oxygen source, the oxygen concentration of the breathing gas may be adjusted. The additional gas from the gas source 1001 is, for example, introduced into the breathing gas line of the gas module 100 via a valve 103. Provision may be made that at least one gas sensor, by means of which the gas concentration of the gas of the gas source 1001 in the breathing gas can be determined, is arranged in the gas module 100.

In addition, a mixing region that ensures better mixing of the breathing gas with the gas added from the gas source 1001 may also be provided in the region of the valve 103.

Figure 3:
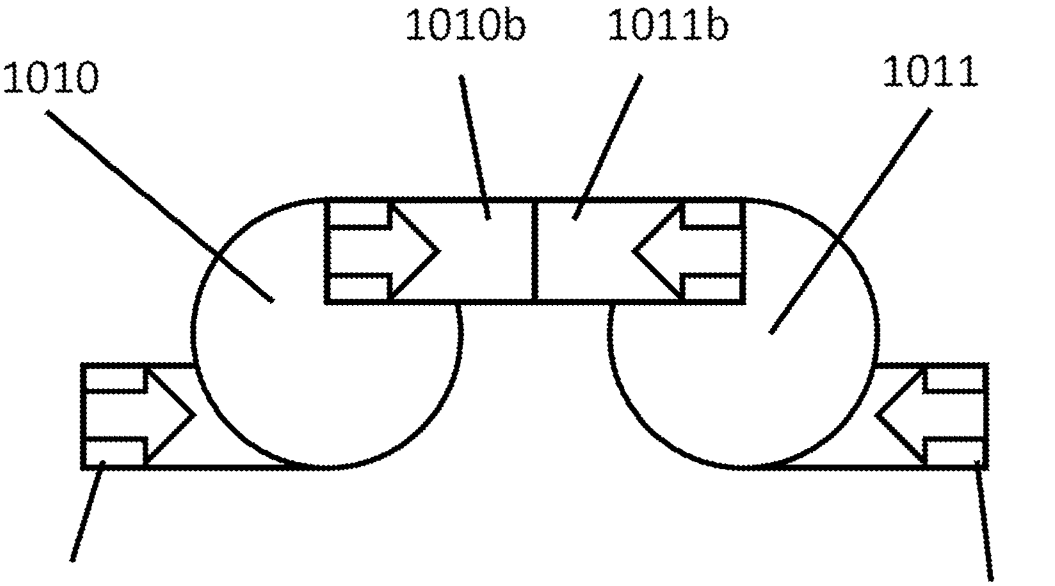
FIGS. 3 a) and b) schematically show two possible arrangements of the blowers of the ventilator of the invention.
Figure 3:
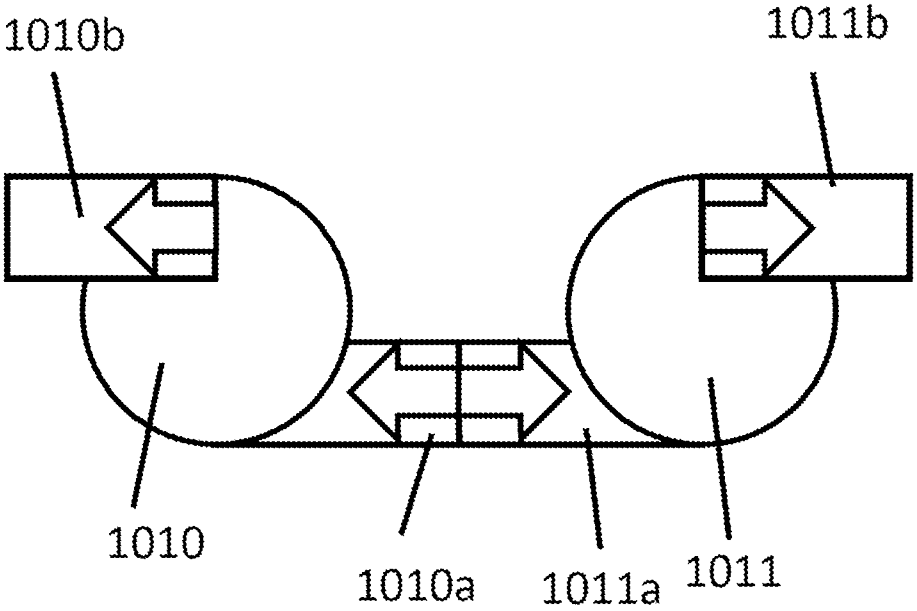

FIGS. 3 *a*) and *b*) schematically represent two possible arrangements of the blowers 1010, 1011 with respect to one another. In the variant of FIG. 3 *a*), the two blowers 1010, 1011 are connected to one another via the respective outlet ports 1010*b*, 1011*b*. The blower 1010 thus takes in gas via the intake port 1010*a* and delivers it through the outlet port 1010*b* into or through the blower 1011, so long as the pressure generated by the blower 1010 overcomes the counter pressure which in some embodiments is generated at least partially by the blower 1011. If gas is intended to be delivered in the opposite direction and/or an opposite pressure is intended to be generated, provision is made that the blower 1011 generates a pressure that overcomes a possibly existing counter pressure (for example due to a slowly running blower 1010). In this case, gas is taken in by the blower 1011 through the intake port 1011*a* and delivered through the blower 1010 via the outlet port 1011*b*.

FIG. 3 *b*) shows a reverse arrangement of the blowers 1010, 1011. The blowers 1010, 1011 are in this case connected via the respective intake ports 1010*a*, 1011*a*. In order to generate a pressure on the side of the outlet port 1010*b* of the blower 1010, gas is taken in by the blower 1010 through the blower 1011, in which case at least any counter pressure generated by the blower 1011 needs to be overcome. The situation is similar when a positive pressure is intended to be generated on the side of the outlet port 1011*b* of the blower 1011, except that in this case the blower 1011 takes in the gas through the blower 1010 and any corresponding counter pressure needs to be overcome.

LIST OF REFERENCE SIGNS

1 ventilator
100 gas module
103 valve
105 connector
200 control module
201 control unit
202 calculation unit
203 evaluation unit
204 sensor unit
205 input unit
206 memory unit
207 user interface
800 hose connection
900 patient
1001 gas source
1005 pressure sensor
1006 flow sensor
1007 temperature sensor
1008 pressure sensor
1010 blower
1010*a* intake port
1010*b* outlet port
1011 blower
1011*a* intake port
1011*b* outlet port
1014 outlet

What is claimed is:

1. A ventilator for the ventilation of a living being, wherein the ventilator comprises at least a gas module and a control module, the gas module comprising at least a first blower and a second blower for generating a positive pressure and/or a negative pressure and at least one connector for connection to a hose, and the control module comprising at least a control unit for controlling the gas module, wherein the first blower has an opposite delivery direction to the second blower, and wherein (i) the first blower and the second blower are connected to one another via their outlet ports; or (ii) the first blower and the second blower are connected to one another via their intake ports.

2. The ventilator of claim 1, wherein the first blower and the second blower are connected to one another via their outlet ports.

3. The ventilator of claim 1, wherein the first blower and the second blower are connected to one another via their intake ports.

4. The ventilator of claim 3, wherein the first blower is arranged so that the first blower at least temporarily generates a positive pressure on a side of the connector and the second blower is arranged so that the second blower at least temporarily generates a negative pressure on the side of the connector.

5. The ventilator of claim 3, wherein during generation of a positive pressure on a side of the connector by at least one of the first and second blowers, the second blower with an opposite delivery direction is off and/or runs at a rotational speed that is less than a rotational speed of the first blower and/or generates a lower pressure than the first blower.

6. The ventilator of claim 3, wherein during generation of a negative pressure on a side of the connector by at least one of the first and second blowers, the first blower with an opposite delivery direction is off and/or runs at a rotational speed that is less than a rotational speed of the second blower and/or generates a lower pressure than the second blower.

7. The ventilator of claim 2, wherein the first blower is arranged so that the first blower at least temporarily generates a negative pressure on a side of the connector and the second blower is arranged so that second blower at least temporarily generates a positive pressure on the side of the connector.

8. The ventilator of claim 7, wherein during generation of a negative pressure on the side of the connector by the first blower, the second blower with an opposite delivery direction is off and/or runs at a rotational speed that is less than a rotational speed of the first blower and/or generates a lower pressure than the first blower.

9. The ventilator of claim 7, wherein during generation of a positive pressure on the side of the connector by the second blower, the first blower with an opposite delivery direction is off and/or runs at a rotational speed that is less than a rotational speed of the second blower and/or generates a lower pressure than the second blower.

10. The ventilator of claim 1, wherein at least one of the first and second blowers is adapted to be capable of generating a negative pressure.

11. The ventilator of claim 1, wherein the ventilator is adapted to be capable of providing ventilation with a negative expiratory pressure.

12. The ventilator of claim 1, wherein the ventilator is adapted to be capable of generating a constant expiratory flow, a negative expiratory pressure being provided by one of the first and second blowers in the course of expiration.

13. The ventilator of claim 1, wherein the ventilator is adapted to be capable of carrying out a cough therapy, a patient being provided with a breathing gas at positive pressure by the first blower during the inspiration, and after an end of the inspiration a rapid switchover being made to a breathing gas at negative pressure, provided by the second blower.

14. The ventilator of claim 1, wherein the ventilator is adapted to be capable of providing superimposed and/or oscillating ventilation.

15. The ventilator of claim 1, wherein the first blower determines a ventilation frequency and the second blower generates a superimposed frequency.

16. The ventilator of claim 14, wherein the first blower determines a ventilation frequency and the second blower generates a superimposed frequency.

17. The ventilator of claim 1, wherein the ventilator is adapted to be capable of providing superimposed ventilation and ventilation with a negative expiratory pressure simultaneously.

18. The ventilator of claim 1, wherein at least one gas source is arranged between the connector and the first and second blowers, at least one gas from the at least one gas source being introduced via at least one valve into a breathing gas delivered by one of the first and second blowers.

19. A method of ventilating a living being, wherein the method comprises ventilating the living being with the ventilator of claim 1.

* * * * *